United States Patent [19]

Williams et al.

[11] Patent Number: 5,504,173

[45] Date of Patent: Apr. 2, 1996

[54] CHEMICAL PROCESS

[75] Inventors: Alfred G. Williams, Binfield; Nicholas R. Foster, Bracknell, both of England

[73] Assignee: Zeneca Limited, London, United Kingdom

[21] Appl. No.: 382,043

[22] PCT Filed: Jul. 28, 1993

[86] PCT No.: PCT/GB93/01592

§ 371 Date: Feb. 9, 1995

§ 102(e) Date: Feb. 9, 1995

[87] PCT Pub. No.: WO94/05620

PCT Pub. Date: Mar. 17, 1994

[30] Foreign Application Priority Data

Aug. 27, 1992 [GB] United Kingdom ............ 9218242

[51] Int. Cl.$^6$ ............ C08G 79/08; C07C 22/00; C08C 19/12
[52] U.S. Cl. ............ 528/4; 525/356; 525/359.2; 525/359.4; 525/359.6; 570/185; 570/189; 570/201; 570/253
[58] Field of Search ............ 570/185, 189, 570/201, 253; 528/4; 525/356, 359.2, 359.4, 359.6

[56] References Cited

U.S. PATENT DOCUMENTS

| 4,446,075 | 5/1984 | Eiglmeier et al. | 260/465 |
| 4,697,017 | 9/1987 | Megyeri et al. | 544/346 |
| 5,332,752 | 7/1994 | Cliff et al. | 514/369 |
| 5,334,748 | 8/1994 | Buckley et al. | 560/60 |
| 5,371,084 | 12/1994 | de Fraine et al. | 514/241 |

OTHER PUBLICATIONS

"Journal of Organic Chemistry" pp. 929–931, vol. 51 Mar. 21, 1986, Sket et al.

Primary Examiner—Melvyn I. Marquis
Assistant Examiner—Randy Gulakowski
Attorney, Agent, or Firm—Marian T. Thomson

[57] ABSTRACT

Process for preparing the (E)-isomer of a compound (II) by contacting the (E) or (Z) isomer of the 2-methylphenyl precursor, or a mixture of both, with bromine in an organic solvent, in the presence of a polymeric base and light.

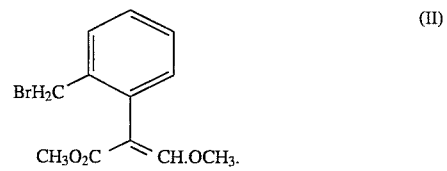

(II)

10 Claims, No Drawings

CHEMICAL PROCESS

This invention relates to a bromination process and more particularly to a process for the bromination of methyl 2-(2-methylphenyl)-3-methoxypropenoate.

A process for brominating (E)-methyl 2-(2-methylphenyl)-3-methoxypropenoate with bromine in chloroform in the presence of azodiisobutyronitrile and light is described in EP-A-0278595. A process for brominating (Z)-methyl 2-(2-methylphenyl)-3-methoxypropenoate to form (E)-methyl 2-(2-bromomethylphenyl)-3-methoxypropenoate using N-bromosuccinimide is described in EP-A-0299694. The side chain bromination of aromatic molecules with a bromine complex of poly(styrene-co-4-vinylpyridine) is described in J. Org. Chem. 1986, 51, 929–931.

According to the present invention there is provided an improved process for preparing a compound of formula (I) which comprises contacting with bromine the (E)- or (Z)-isomer of a compound of formula (II) or a mixture of both isomers, in an inert organic solvent, in the presence of a polymeric base (as hereinafter defined) and light.

By "inert organic solvent" is meant an organic solvent which does not react chemically to any significant extent with bromine under the conditions of the process. Suitable solvents include halogenated, for example chlorinated, aliphatic and aromatic organic solvents having a boiling point not less than 20° C., for instance carbon tetrachloride and chlorobenzene.

By the term "polymeric base" is meant an organic polymer comprising repeat units containing a basic group which will form a salt with an inorganic acid, in this case hydrogen bromide, without generating water. For example, the basic group may be an amino group, such as a tertiary amino group. Typically the polymeric base will comprise repeat units containing a tertiary nitrogen atom which is a member of a heterocyclic ring. The heterocyclic ring may be aromatic, for example a pyridine ring, or non-aromatic, for example, a pyrrolidine ring. Suitable polymeric bases include cross-linked poly(vinylpyridine) polymers, cross-linked copolymers of styrene and vinylpyridine, for instance 4-vinylpyridine, and poly(N-vinylpyrrolidone) polymers. Commercially available examples include poly(4-vinylpyridine) 2% cross-linked with divinylbenzene, poly(2-vinylpyridine-co-styrene) having a styrene content of 30%; poly(4-vinylpyridine-co-styrene) having a styrene content of 10%; polyvinylpyrrolidone, cross-linked (PVPDC) mp>300° C.; and polyvinylpyrrolidone (povidone, PVP) of varying average molecular weights of 10,000, 24,000, 40,000 and 360,000. Ideally, the polymeric base should be insoluble in the solvent under the conditions of the process, thereby facilitating recovery after use. The recovered polymeric material may then be regenerated by treatment with, for example, an aqueous base and dried ready for re-use.

The process of the invention is suitably carried out at a temperature of from 20° C. to 80° C., typically from 25° C. to 75° C., but may be limited by the boiling point of the solvent used. Examples of suitable operating temperatures are 55° C. to 70° C., for instance 60° C. to 65° C. or 65° C. to 70° C., and 20° C. to 25° C.

The process of the invention is conveniently carried out by the slow, for example dropwise, addition of bromine to a stirred mixture of the compound (II) and the pre-dried polymeric base in the inert organic solvent whilst irradiating the mixture with visible light. The visible light may be supplied by a tungsten-halogen lamp.

The starting materials, which may be the (E)- or (Z)-isomers of compound (II) or a mixture of both, and their methods of preparation are already described in the chemical literature. For example, the preparation of (E)-methyl 2-(2-methylphenyl)-3-methoxypropenoate is described in EP-A-0203606 and the preparation of the (Z)-isomer is described in EP-A-0299694.

The invention provides a high-yielding process for an intermediate chemical useful in the manufacture of fungicides of the type described in, for example, EP-A-0370629.

The invention is illustrated by the following examples in which solutions, when dried, were dried over magnesium sulphate and, when concentrated, were concentrated under reduced pressure. Materials were dried before use, as appropriate. Where shown, infrared and NMR data are selective. No attempt is made to list every absorption in all cases. $^1$H NMR spectra were recorded using $CDCl_3$ solutions unless otherwise stated. The following abbreviations are used throughout:

m.p.=melting point
GC=gas chromatography
HPLC=High performance liquid chromatography
NMR=nuclear magnetic resonence
IR=infrared

EXAMPLE 1

This Example illustrates the preparation of (E)-methyl 2-[2 -(bromomethyl)phenyl-3-methoxypropenoate, using poly(vinylpyrrolidone) in carbon tetrachloride at 60° C. to 62° C.

Bromine (178 ml) was added over 5.25 hours to a stirred mixture of (E)-methyl 3-methoxy-2-(2-methylphenyl)propenoate (309 g) and poly(vinylpyrrolidone) (cross-linked, m.p.>300° C. ex Aldrich Chemical Co. Ltd.; pre-dried by vacuum drying, 534 g) in carbon tetrachloride (1750 ml), whilst irradiating at 60° C. to 62° C. with two 500 watt tungsten-halogen lamps.

After a further 5 hours irradiation at 60° C. to 62° C., the reaction mixture was cooled to room temperature and solid material was filtered off and washed with dichloromethane. The combined filtrates were concentrated to give a pale yellow crystalline solid (403 g).

Recrystallisation from cyclohexane yielded a white powder (234 g), m.p. 88° C. to 91° C.; IR (Nujol): 1704, 1627 cm$^{-1}$ ; $^1$H NMR (270 MHz) δ: 3.70(3H,s), 3.83(3H,s), 4.41(2H,s), 7.1–7.6(4H,m), 7.64(1H,s)ppm.

EXAMPLE 2

This Example illustrates the preparation (E)-methyl 2-[2-(bromomethyl)phenyl]-3-methoxypropenoate using poly(4-vinylpyridine) in carbon tetrachloride at 65° C.

Bromine (37 ml) was added over 6.5 hours to a stirred mixture of (E)-methyl 3-methoxy-2-(2-methylphenyl)propenoate (103 g) and poly(4-vinylpyridine) (2% cross-linked with divinylbenzene, 100–200 mesh, ex Fluka Chemie AG: pre-dried by azeotropic distillation/vacuum drying, 153 g) in carbon tetrachloride (380 ml), whilst irradiating at 65° C. with a 500 watt tungsten-halogen lamp.

After a further 7 hours irradiation at 65° C. the reaction mixture was cooled to room temperature and solid material was filtered off and washed with carbon tetrachloride. The combined filtrates were dried and concentrated to give a pale yellow waxy solid (146 g), 78% pure by GC. Recrystallisation from isopropanol yielded a white powder (90 g), the major component (96%) of which had an identical GC retention time to the material prepared in Example 1.

EXAMPLE 3

This Example illustrates the preparation of (E)-methyl 2-[2-(bromomethyl)phenyl]-3-methoxypropenoate, using poly(vinylpyrrolidone) in chlorobenzene at 63° C. to 67° C.

Bromine (3 ml) was added over 95 minutes to a stirred mixture of (E)-methyl 3-methoxy-2-(2-methylphenyl)propenoate (5.05 g) and poly(vinylpyrrolidone) (cross-linked, m.p.>300° C. ex Aldrich Chemical Co. Ltd.; pre-dried by vacuum drying, 8.7 g) in chlorobenzene (45 ml), containing Synperonic NP13 surfactant (0.05 ml), whilst irradiating at 63° C. to 67° C. with a 500 watt tungsten-halogen lamp.

After a further 5.75 hours irradiation at 63° C. to 67° C., the reaction mixture was cooled to room temperature and solid material was filtered off and washed with chlorobenzene.

The combined filtrates were concentrated to give an orange oil (6.5 g), slowly crystallising on standing, whose major component (68%) had an identical GC retention time to the material prepared as described in Example 1.

Trituration in a cyclohexane/diethyl ether mixture yielded a cream solid (2.42 g), where the major component was 94.4% by GC, with identical GC and HPLC retention times to the material from Example 1; m.p. 86° C. to 89° C.; IR (Nujol):1704, 1627 cm$^{-1}$.

EXAMPLE 4

This Example illustrates the preparation of (E)-methyl 2-[2-(bromomethyl)phenyl]-3-methoxypropenoate using poly(vinylpyrrolidone) in chlorobenzene at 21° C. to 24° C.

Bromine (3 ml) was added over 100 minutes to a stirred mixture of (E)-methyl 3-methoxy-2-(2-methylphenyl)propenoate (5.05 g) and poly(vinylpyrrolidone) (cross-linked, m.p.>300° C. ex Aldrich Chemical Co. Ltd.; pre-dried by vacuum drying, 8.7 g) in chlorobenzene (45 ml), containing Synperonic NP13 surfactant (0.05 ml), whilst irradiating at 21° C. to 24° C. with a 500 watt tungsten-halogen lamp.

After a further 6.25 hours irradiation at 21° C. to 24° C., the reaction mixture was cooled to room temperature and solid material was filtered off and washed with chlorobenzene.

The combined filtrates were concentrated to give an orange oil (6.84 g), slowly crystallising on standing, whose major component (64.5%) had an identical GC retention time to the material prepared in Example 1.

Trituration in a cyclohexane/diethyl ether mixture yielded a white powder (1.62 g), where the major component was 91% by GO, with identical GO and HPLC retention times to the material from Example 1; m.p. 85.5° C. to 88° C.; IR (Nujol):1704, 1627cm$^{-1}$.

Chemical Formulae
(in description)

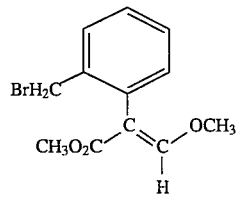
(I)

-continued
Chemical Formulae
(in description)

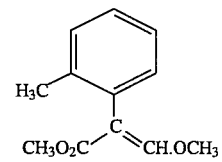
(II)

We claim:

1. A process for preparing a compound of formula (I):

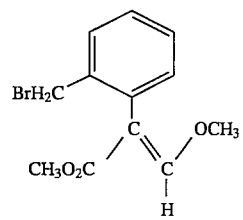
(I)

which comprises contacting with bromine the (E)- or (Z)-isomer of a compound of formula (II):

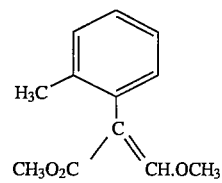
(II)

or a mixture of both isomers, in an inert organic solvent, in the presence of a polymeric base and light, the polymeric base being an organic polymer comprising repeat units containing a basic group which will form a salt with hydrogen bromide without generating water.

2. A process according to claim 1 in which the organic solvent is a chlorinated aliphatic or aromatic organic solvent having a boiling point not less than 20° C.

3. A process according to claim 1 in which the organic solvent is carbon tetrachloride or chlorobenzene.

4. A process according to claim 1 in which the polymeric base comprises repeat units containing a tertiary nitrogen atom which is a member of a heterocyclic ring.

5. A process according to claim 4 in which the heterocyclic ring is a pyridine or pyrrolidone ring.

6. A process according to claim 1 in which the polymeric base is a cross-linked polyvinylpyridine polymer, a cross-linked copolymer of styrene and vinylpyridine or a poly(N-vinylpyrrolidone) polymer.

7. A process according to claim 1 in which the polymeric base is a poly(4-vinylpyridine) or polyvinylpyrrolidone polymer.

8. A process according to claim 1 in which the compound of formula (II) is contacted with bromine at a temperature of from 20° C. to 80° C.

9. A process according to claim 8 in which the temperature is from 55° C. to 70° C.

10. A process according to claim 8 in which the temperature is from 20° C. to 25° C.

* * * * *